United States Patent [19]

Greco et al.

[11] Patent Number: 4,743,631

[45] Date of Patent: May 10, 1988

[54] ACRYLATED PHOSPHONOACETIC ACIDS AS ADHESION PROMOTERS, METHOD FOR MAKING, AND CURABLE COATINGS FOR METAL

[75] Inventors: Alberto Greco, Dresano; Renato Butturini, Induno Olona; Sergio Arrighetti, S. Donato Milanese, all of Italy

[73] Assignee: Enichem Sintesi S.p.A., Palermo, Italy

[21] Appl. No.: 773,418

[22] Filed: Sep. 6, 1985

[30] Foreign Application Priority Data

Sep. 20, 1984 [IT] Italy .............................. 22734 A/84

[51] Int. Cl.⁴ .................... C07F 9/02; C08F 230/02; C08F 283/01; C08F 283/02
[52] U.S. Cl. ................... 522/107; 252/182.14; 522/171; 525/34; 525/37; 528/279; 528/289; 528/304; 558/105; 558/180; 526/278
[58] Field of Search .................. 526/278; 522/171; 558/105, 180; 252/188.31

[56] References Cited

U.S. PATENT DOCUMENTS

| | | | |
|---|---|---|---|
| 2,867,610 | 1/1959 | Toy | 526/278 |
| 2,957,931 | 10/1960 | Hamilton | 522/171 |
| 3,256,191 | 6/1966 | Reed | 558/180 |
| 3,754,972 | 8/1973 | de Majistre | 528/272 |
| 3,855,364 | 12/1974 | Steckler | 558/180 |
| 3,957,918 | 5/1976 | Dickie | 558/180 |
| 4,016,222 | 4/1977 | Dursch | 558/180 |
| 4,222,780 | 9/1980 | Shibatani | 526/278 |
| 4,259,117 | 3/1981 | Yamauchi | 526/278 |

*Primary Examiner*—John C. Bleutge
*Assistant Examiner*—Arthur H. Koeckert
*Attorney, Agent, or Firm*—Hedman, Gibson, Costigan & Hoare

[57] ABSTRACT

Adhesion promoters for metal substrates for paints cross-linkable with U.V. or E.B. radiations or with peroxides of general formula:

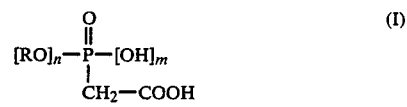

(wherein R, m and n have the meaning which we will specify in the disclosure), obtained by means of the reaction of glycidyl acrylate and/or glycidyl methacrylate with dihydrophosphonoacetic acid.

16 Claims, No Drawings

ACRYLATED PHOSPHONOACETIC ACIDS AS ADHESION PROMOTERS, METHOD FOR MAKING, AND CURABLE COATINGS FOR METAL

The present invention relates to the preparation of photo-crosslinkable paints obtained by means of the reaction of glycidyl derivatives of acrylic (methacrylic) acid with phosphonoacetic acid, and to their use as adhesion promoters for metal substrates in combination with paints crosslinkable with U.V. or E.B. radiations or with peroxides.

One method to produce coatings having good adhesion characteristics consists in adding to the paint crosslinkable with U.V. or E.B. radiations or with a peroxide, an ester of general formula

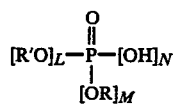

(wherein R', R, L, M, N have the meaning as reported in U.K. Pat. No. 1393545) to the purpose of favouring the adhesion between the paint and the metal substrate, in that it is known indeed that the paints crosslinkable by means of radiations have a poor adhesion to metals. However, the so-obtained coatings, due to the fact that they contain a strongly acidic adhesion promoter, are easily prone to be corroded in a moist environment. Such interface corrosion phenomena are causes of adhesion loss whenever the coated item is exposed to moisture.

We have now found a new class of adhesion promoters, which improve the prior state of the art, in that whilst on one side they introduce polar enough groups, suitable to improve the adhesion at the metal-paint interface, on the other they do not increase the corrosion-due phenomena to a very notable extent.

This class of adhesion promoters on the basis of compounds derivatives of phosphonylacetic acid obviate the negative effects typical of the esters of phosphoric acid, e.g., the increase in corrosion sensitivity, in that they combine a lower absolute acidity with the presence of two adjacent acidic hydroxy groups, one inorganic and the other one of organic character, in an arrangement capable of chelating metal ions.

It is therefore a first object of the present patent application a new class of compounds of general formula (I):

$$[RO]_n-\overset{O}{\underset{CH_2COOH}{P}}-[OH]_m \quad (I)$$

wherein:

R = 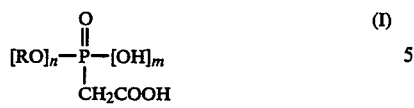 and/or

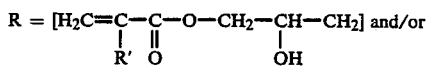

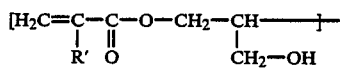

R' = H and/or $CH_3$, $n = 1$ or 2,
$m = 1$ or 0.

A second object of the present patent application is a method for the synthesis of compounds of general formula (I): they are prepared indeed by means of the reaction of glycidyl acrylate (GA) and/or glycidyl methacrylate (GMA) with dihydroxyphosphonoacetic acid (DHPAA).

The reaction is generally carried out with GA and/or GMA/DHPAA ratios comprised within the range of from 1.20 to 1.85 [$1.20 \leq$ GA and/or GMA/DHPAA $\leq 1.85$] and preferably of from 1.35 to 1.60 [$1.35 \leq$ GA and/or GMA/DHPAA $\leq 1.60$].

The reaction does not require catalysts, and can be carried out either in bulk or in solution. When carried out in solution, it is carried out in the presence of a suitable solvent, generally in tetrahydrofuran. The reaction temperature is comprised within the range of from 20° to 140° C. ($20 \leq T \leq 140°$ C.), preferably of from 60° to 100° C. [$60 \leq T \leq 100°$ C.].

The reaction is preferably carried out by adding GA and/or GMA to DHPAA, with temperature controlling.

It is preferable to add to the reaction mixture a polymerization inhibitor in amounts ranging from 0.01 to 1% by weight [$0.01 \leq p \leq 1\%$ by weight], preferably of from 0.1 to 0.5% by weight [$0.1 \leq p \leq 0.5\%$ by weight]. The inhibitor is generally selected from hydroquinone and its derivatives, such as e.g. toluquinone, hydroquinone monomethyl ether and so forth.

The compounds of general formula (I) are obtained with quantitative yields, they hence do not require any further purifications, if the reaction is carried out in solution, the solvent is however distilled off under reduced pressure and at a temperature lower than 70° C. [$T \leq 70°$ C.], preferably than 40° C. [$T \leq 40°$ C.].

The product (I) is soluble in the common organic solvents and also in the acrylic monomers.

The product (I) can be stored, after its synthesis, either as pure product, or as diluted in acrylic oligomers [10–50% by weight relatively to the compound (1)], preferably selected from butanediol diacrylate, hexanediol diacrylate, diethylene glycol diacrylate.

It is a last object of the present patent application the use of the compounds of general formula (I) as adhesion promoters for metal substrates for paints crosslinkable with U.V. or E.B. radiations, or with peroxides.

The metal substrates which are pretreated with the adhesion promoters which are the object of the present patent application are preferably on the basis of iron or of alloys thereof, of aluminum or of copper. The paints crosslinkable with U.V. or E.B. radiations or with peroxides are selected from
acrylate polyester paints
maleate polyester paints
acrylate acrylic paints
acrylate urethane paints
diallylphthalate paints
acrylate silicone paints.

The compound of formula (I) is generally used in amounts lower than 10% by weight [$p \leq 10\%$ by weight] relatively to the paint, preferably within the range of from 1 to 5% by weight [$1 \leq P \leq 5\%$ by weight].

EXAMPLES

Example No. 1

Inside a 4-neck flask of 250 ml in volume, provided with nitrogen inlet, thermometer, reflux condenser, loading funnel and magnetic bar stirrer, phosphonylacetic acid (30 g, 214.3 mmol) was dissolved in THF (100 ml) containing methylhydroquinone (5 mg) and phenothiazine (5 mg) at the temperature of +65° C. While keeping the solution stirred, from the dropping funnel glycidyl acrylate (35.58 g, 32.5 ml, 282 mmol) was added dropwise over about one hour. As soon as the addition was ended, the temperature of the flask was increased to +80° C., and the stirring was continued for further two hours.

From the resulting resin THF was removed by the rotary evaporator, at +38° C. and under 0.5 torr. It was a very viscous clear oil, with an acidity number of 232 (mg of KOH/g).

A portion of the material underwent photo-crosslinking after addition of DAROCUR ® 1173 (5% by volume), and exposure to a 450 W U.V. lamp at a distance of 15 cm over 60'. More than 90% of material resulted to be insoluble in methylene chloride.

The phosphonic resin obtained is soluble in the usual reactive solvents for crosslinkable paints, and compatible with the solventless paints and with the usual acrylic diluents.

Example No. 2

An unsaturated polyester polycarbonate resin was prepared as follows.

Into a 4-neck flask of 1 liter in capacity, provided with nitrogen inlet, mechanical stirrer and 40-cm Vigreux condenser provided with distilling head, ethylene glycol (66.22 g), glycerol (16.1 g), triethylene glycol (15 g), tri-hydroxymethyl-isocyanurate (59 g), dimethyl terephthalate (104.76 g), diethyl carbonate (28.6 g) and dibutyl-tin oxide (0.75 g) were charged. The flask was dipped inside a heating bath at +200° C., and the reaction was started. After two hours, the development of methanol and of ethanol accompanied by diethyl carbonate had terminated. The bath temperature was then increased to +220° C. over 30', the reaction mass being then kept stirred at this temperature for one hour.

The temperature was reduced to +190° C. and maleic anhydride (37.9 g) was added over about 10'. The temperature of the bath was increased to +200°–205° C., and the reaction was continued until a number of acidity of 10 was reached.

The bath was cooled to +90° C., benzoquinone (0.49 g) was added and, after having interrupted the heating, a mixture of hexanediol diacrylate (122.5 g) and of diethylene glycol diacrylate (122.5 g) was added. After the addition of the photoinitiator (benzoin isopropyl ether, 118 g), the quite thin resulting paint (920 cps at +25° C.) was coated on a steel plate by means of a K-control bar to the nominal thickness of 35μ, and crosslinked by means of 20 passes at a space speed of 25 m/sec under nitrogen by means of a mercury vapour lamp of 80 watts/cm in power.

This coating showed complete lack of adhesion at the adhesion test carried out by crosshatching and adhesive tape peeling (ASTM D 3002).

To two different portions of the paint 3 and 5% by weight of the adhesion promoter as specified in Example N. 1 was added, and two steel plates were then coated and crosslinked under the same conditions as specified above. In both samples a complete adhesion (100%) was achieved when the previously indicated test was repeated.

The plates which had passed the adhesion test were plunged into demineralized water, at room temperature (+25° C.) for 24 hours, after having been hemmed with adhesive tape.

At the end of this time no blistering was detectable and the adhesion was retained. To comparison purposes, two different samples of the same paint were loaded with 3 and 5% by weight of the acrylate phosphoric ester, and after having been coated onto steel plates, they underwent crosslinking under the same conditions as already mentioned. The so-obtained paint passed the adhesion test (ASTM D 3002), however when the plates were dipped for 24 hours into demineralized water at room temperature (+25° C.), blistering was apparent on the surface, and the adhesion test gave complete failing results (100% peeling off).

Example No. 3

Phosphonoacetic acid triethylester (65.5 g, 0.292 mol) in 35% conc. hydrochloric acid (150 ml) was gently refluxed over 6 hours, at the end of which water and hydrochloric acid were evaporated off at 90°–100° C. under a reduced vacuum (water pump).

To the thick liquid obtained, 80/20 (by volume) toluene/ethanol (100 ml) was added, and the mass was stripped again at 90°–100° C. on the water pump, to yield 35.5 g of viscous clear syrup, containing 0.5% of chlorine, corresponding to 0.254, moles (86.8% yield) of:

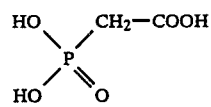

This syrup was diluted in peroxide-free anhydrous THF containing 0.2 g of hydroquinone, and to the mass glycidyl acrylate (40 ml, 44.8 g, 0.347 mol) was added, the addition rate being so adjusted as to keep the temperature comprised within the range of from +75° C. to +90° C. This step required a time of 20–30', and some care had to be taken to withdraw the reaction heat. When the reaction had ended, a further portion of glycidyl acrylate (5 ml, 5.56 g, 0.04 mol) was added, and the reaction was continued for further 30'at +75° C. Twenty ml of diethylene glycol diacrylate were then added, and THF was distilled off in vacuo at +40° C.

From the flask, 105 g of product were recovered, of which the product of formula (I) constituted about 80%.

Example No. 4

An unsaturated polyester resin was prepared as follows:

Into a 4-neck flask of 1 liter in volume, equipped with nitrogen inlet, mechanical stirrer and 40-cm long Vigreux condenser provided with distillation head, ethylene glycol (66.22 g), glycerol (16.1 g), triethylene glycol (15 g), trihydroxyethyl isocyanurate (59 g), dimethylterephthalate (28.6 g) and titanium isopropoxide (0.85 ml) were loaded.

The flask was then dipped into a bath at +200° C., and the stirring was started. The reaction was continued until the development of ethanol and of methanol had ended (2 hours); at this time, the bath temperature was decreased down to +190° C. and dibutyltin oxide (0.6 g) and maleic anhydride (37.9 g) was added. The temperature was increased again to +200°-250° C., and the reaction was continued up to a number of acidity of 8, the bath was cooled down to +100° C., and hydroquinone monomethyl ether (0.5 g) was added, and the mass was finally diluted to 50% of solids in the following reactive solvents:

| | |
|---|---|
| hexanediol diacrylate | 90 ml |
| vinylpyrrolidone | 90 ml |
| diethylene glycol diacrylate | 50 ml. |

To a portion of said paint, a photosensitizer (4% by weight of Darocur ® 1173) was added, and the paint was coated to a thickness of 12μ on a plate of common steel.

The adhesion (tape) test gave complete failure. A similar test, carried out with 2.5% of the resin as of Example N. 3 above described gave a total adhesion.

We claim:

1. A process for the synthesis of an adhesion promoter composition, consisting of reacting glycidyl acrylate and/or glycidyl methacrylate with dihydroxyphosphonoacetic acid to provide a mixture of compounds having the formulas:

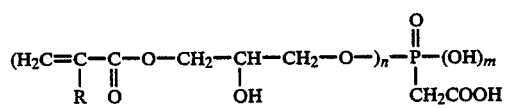

and

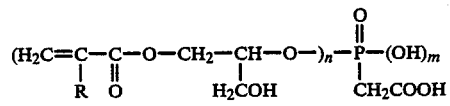

wherein R is, independently, hydrogen or methyl; n is 1 or 2; and m is 0 or 1.

2. A process according to claim 1, wherein the ratio of glycidyl acrylate and/or glycidyl methacrylate to dihydroxyphosphonoacetic acid is from 1.20 to 1.85.

3. A process according to claim 2, wherein the ratio of glycidyl acrylate and/or glycidyl methacrylate to dihydroxyphosphonoacetic acid is from 1.35 to 1.60, respectively.

4. A process according to claim 1, wherein the process is carried out at a temperature of from 20° to 140° C., inclusive.

5. A process according to claim 4, wherein the reaction is carried out at temperatures of from 60° to 100° C., inclusive.

6. A process according to claim 1, wherein the reaction is carried out in the presence of a polymerization inhibitor.

7. A process according to claim 6, wherein the polymerization inhibitor is selected from the group consisting of hydroquinone, hydroquinone monomethyl ether, toluquinone.

8. A process according to claim 6, wherein the polymerization inhibitor is present in amounts of from 0.01 to 1% by weight, inclusive.

9. A process according to claim 8, the polymerization inhibitor is present in amounts of from 0.1 to 0.5% by weight, inclusive.

10. A process according to claim 1, wherein the reaction is carried out in a solvent.

11. A process according to claim 10, wherein the solvent is tetrahydrofuran.

12. An adhesion promoter composition comprising a mixture of compounds having the formulas:

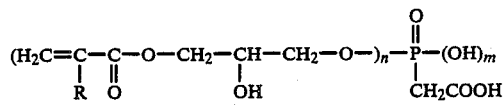

and

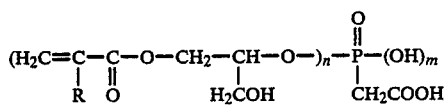

wherein R is, independently, hydrogen or methyl; n is 1 or 2; and m is 0 or 1.

13. An adhesion promoter composition according to claim 12, prepared by reacting dihydroxyphosphonoacetic acid with glycidyl acrylate, glycidyl methacrylate, or a mixture thereof.

14. A protective coating composition having good adhesion to metal substrates comprising a radiation-curable or peroxide-curable paint and an adhesion promoter composition comprising a mixture of compounds having the formulas:

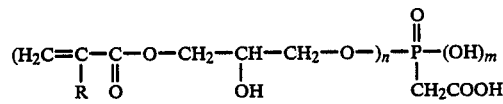

and

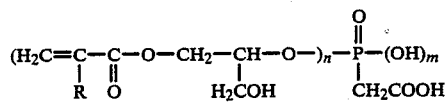

wherein R is, independently, hydrogen or methyl; n is 1 or 2; and m is 0 or 1.

15. A coating composition as defined in claim 14, wherein said adhesion promoter composition comprises less than about 10% by weight, based on the weight of the paint.

16. A coating composition as defined in claim 14, wherein the adhesion promoter composition comprises from 1 to 3% by weight, based on the weight of the paint.

* * * * *